(12) United States Patent
Schwartz et al.

(10) Patent No.: US 12,396,861 B2
(45) Date of Patent: Aug. 26, 2025

(54) IMPLANT SYSTEMS FOR REPAIR OF A GLENOID CAVITY

(71) Applicant: BIOPOLY, LLC, Fort Wayne, IN (US)

(72) Inventors: Herbert E. Schwartz, Fort Wayne, IN (US); Matthew L. Mroczkowski, Fort Wayne, IN (US)

(73) Assignee: BioPoly, LLC, Fort Wayne, IN (US)

( * ) Notice: Subject to any disclaimer, the term of this patent is extended or adjusted under 35 U.S.C. 154(b) by 952 days.

(21) Appl. No.: 17/375,705

(22) Filed: Jul. 14, 2021

(65) Prior Publication Data
US 2021/0338445 A1 Nov. 4, 2021

Related U.S. Application Data

(63) Continuation of application No. PCT/US2020/013484, filed on Jan. 14, 2020.
(Continued)

(51) Int. Cl.
*A61F 2/40* (2006.01)
*A61B 17/16* (2006.01)
(Continued)

(52) U.S. Cl.
CPC ........ *A61F 2/4081* (2013.01); *A61B 17/1684* (2013.01); *A61B 17/1778* (2016.11);
(Continued)

(58) Field of Classification Search
CPC .......... A61F 2/4081; A61F 2002/30574; A61F 2002/4085; A61F 2310/00011; A61B 17/1684; A61B 17/1778; A61B 17/15
See application file for complete search history.

(56) References Cited

U.S. PATENT DOCUMENTS 6,383,224 B1 5/2002 Gie et al.
6,629,997 B2 10/2003 Mansmann
(Continued)

FOREIGN PATENT DOCUMENTS

WO 2007078978 A2 7/2007
WO 2016151047 A1 9/2016
(Continued)

OTHER PUBLICATIONS

Schwartz et al., U.S. Appl. No. 17/375,701, filed Jul. 14, 2021, entitled "Implant Systems for Repair of a Humeral Head".
(Continued)

*Primary Examiner* — Suzette J Gherbi
(74) *Attorney, Agent, or Firm* — Heslin Rothenberg Farley & Mesiti P.C.

(57) ABSTRACT

A glenoid implant system, for example, includes a glenoid implant and a glenoid cutting guide. The glenoid implant includes a body having a concave surface with a first curved edge portion and a second curved edge portion, and an attachment surface having a concave edge portion joined to the second curved edge portion of the concave surface. The concave surface and the attachment surface are disposed at an angle. The glenoid cutting guide includes a body having a convex surface engageable with a surface of a glenoid cavity and a cutting guide surface for resecting a cutout in a glenoid cavity, the cutout having a curved edge portion corresponding to the second curved edge portion of the glenoid implant.

28 Claims, 11 Drawing Sheets

Related U.S. Application Data

(60) Provisional application No. 62/792,618, filed on Jan. 15, 2019.

(51) Int. Cl.
*A61B 17/17* (2006.01)
*A61F 2/30* (2006.01)

(52) U.S. Cl.
CPC .............. *A61F 2002/30574* (2013.01); *A61F 2002/4085* (2013.01); *A61F 2310/00011* (2013.01)

(56) References Cited

U.S. PATENT DOCUMENTS

| | | | |
|---|---|---|---|
| 6,696,073 B2 | 2/2004 | Boyce et al. | |
| 6,855,167 B2 | 2/2005 | Shimp et al. | |
| 7,060,096 B1 | 6/2006 | Schopf et al. | |
| 7,618,454 B2 | 11/2009 | Bentley et al. | |
| 7,662,954 B2 | 2/2010 | James et al. | |
| 8,002,840 B2 | 8/2011 | Aram et al. | |
| 8,303,967 B2 | 11/2012 | Clineff et al. | |
| 8,506,569 B2 | 8/2013 | Keefer et al. | |
| 8,702,717 B2 | 4/2014 | Rauscher et al. | |
| 9,278,004 B2 | 3/2016 | Shenoy et al. | |
| 9,795,410 B2 | 10/2017 | Shenoy et al. | |
| 10,045,851 B2 | 8/2018 | Grotz | |
| 10,350,078 B2 | 7/2019 | Ek et al. | |
| 10,449,054 B2 | 10/2019 | Hopkins | |
| 10,980,640 B2 | 4/2021 | Chavarria et al. | |
| 11,285,009 B2 | 3/2022 | Terrill | |
| 11,896,476 B2 | 2/2024 | Shulock et al. | |
| 2003/0009235 A1 | 1/2003 | Manrique et al. | |
| 2003/0158605 A1 | 8/2003 | Tornier | |
| 2004/0148026 A1 | 7/2004 | Bonutti | |
| 2004/0267366 A1 | 12/2004 | Kruger | |
| 2005/0049710 A1 | 3/2005 | O'Driscoll et al. | |
| 2005/0182493 A1 | 8/2005 | Bertram, III | |
| 2006/0074430 A1* | 4/2006 | Deffenbaugh | A61F 2/4612 606/87 |
| 2008/0188945 A1 | 8/2008 | Boyce et al. | |
| 2010/0268339 A1 | 10/2010 | Malinin et al. | |
| 2011/0009964 A1 | 1/2011 | Schwartz et al. | |
| 2011/0264153 A1* | 10/2011 | Hassler | A61F 2/4014 606/86 R |
| 2012/0053590 A1 | 3/2012 | Allen et al. | |
| 2012/0283840 A1 | 11/2012 | Frederick et al. | |
| 2013/0184820 A1 | 7/2013 | Schwartz et al. | |
| 2013/0211531 A1 | 8/2013 | Steines et al. | |
| 2013/0238099 A1 | 9/2013 | Hardy et al. | |
| 2014/0257304 A1 | 9/2014 | Eash | |
| 2015/0157462 A1* | 6/2015 | Ek | A61F 2/30734 606/80 |
| 2015/0223941 A1* | 8/2015 | Lang | A61B 17/1778 606/87 |
| 2017/0027708 A1* | 2/2017 | Shenoy | A61B 17/8061 |
| 2017/0224496 A1 | 8/2017 | Witt et al. | |
| 2018/0028202 A1 | 2/2018 | Nelson et al. | |
| 2021/0007858 A1* | 1/2021 | Terrill | A61F 2/4081 |
| 2021/0068968 A1* | 3/2021 | Terrill | A61F 2/30734 |
| 2021/0204967 A1* | 7/2021 | Lefebvre | A61B 17/1778 |
| 2021/0338443 A1 | 11/2021 | Schwartz et al. | |
| 2021/0338445 A1 | 11/2021 | Schwartz et al. | |
| 2022/0000629 A1* | 1/2022 | Mehta | A61F 2/30767 |
| 2024/0008995 A1* | 1/2024 | Gargac | A61B 17/1684 |

FOREIGN PATENT DOCUMENTS

| | | |
|---|---|---|
| WO | 2020150216 A1 | 7/2020 |
| WO | 2020150217 A1 | 7/2020 |

OTHER PUBLICATIONS

International Preliminary Report on Patentability for International Application No. PCT/US2020/013484, dated Jun. 16, 2021, 9 pages, International Bureau of WIPO.

International Search Report and Written Opinion of the International Searching Authority for International Patent Application No. PCT/US2020/013482 mailed on Mar. 19, 2020.

International Search Report and Written Opinion of the International Searching Authority for International Patent Application No. PCT/US2020/013484 mailed on Apr. 6, 2020.

\* cited by examiner

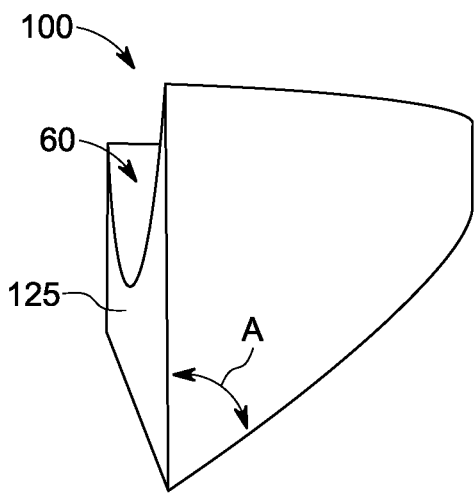
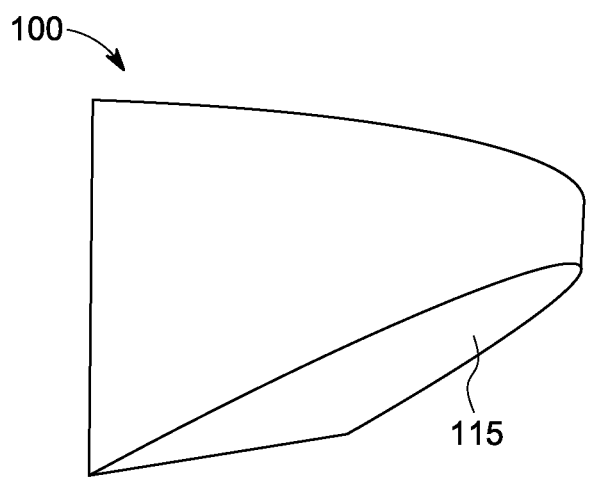
FIG. 9     FIG. 10
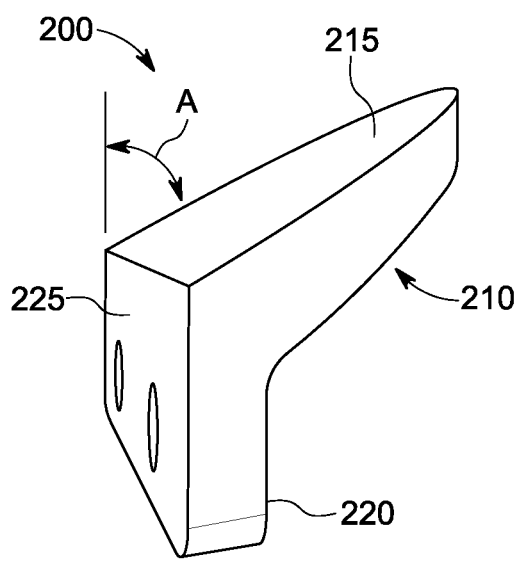
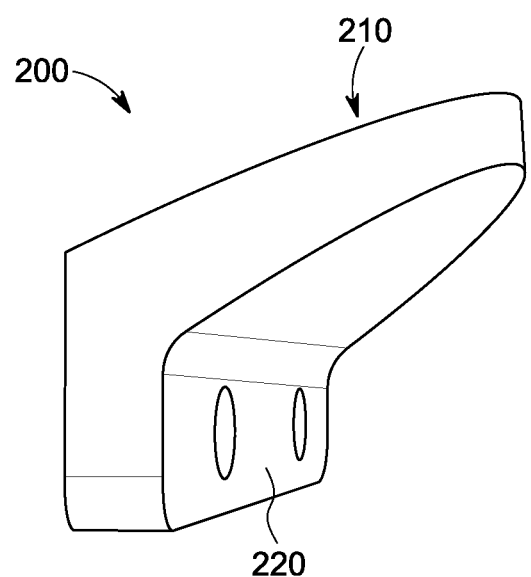
FIG. 11     FIG. 12

IMPLANT SYSTEMS FOR REPAIR OF A GLENOID CAVITY

CLAIM TO PRIORITY APPLICATION

This application is a U.S. National Stage Continuation application based on International Application No. PCT/US2020/013484 filed on Jan. 14, 2020, and claims the priority to U.S. Provisional Application No. 62/792,618 filed on Jan. 15, 2019, entitled "Implant Systems For Repair Of A Glenoid Cavity", which is hereby incorporated herein by reference in its entirety.

CROSS-REFERENCE TO RELATED APPLICATION

This application is related to commonly assigned, co-filed international PCT patent application no: PCT/US2020/013482, filed Jan. 14, 2020, entitled "Implant Systems For Repair Of A Humeral Head" which international PCT patent application claims priority to U.S. provisional patent application No. 62/792,594, filed Jan. 15, 2019, entitled "Implant Systems For Repair Of A Humeral Head", which applications are hereby incorporated herein by reference in their entirety.

FIELD OF THE DISCLOSURE

The present disclosure relates generally to surgical implants for use in repairing a shoulder joint, and more particularly to glenoid implant systems having a glenoid implant and a corresponding glenoid cutting guide for repair of a glenoid cavity.

BACKGROUND

Bankart lesions, on the surface of a glenoid cavity, are often treated with bone graft (e.g., iliac crest) or with a Latarjet surgical technique.

SUMMARY

Shortcomings of the prior art are overcome and additional advantages are provided through the provision, in one embodiment, of a glenoid implant system, which includes, for example, a glenoid implant and a glenoid cutting guide. The glenoid implant includes a body having a concave surface with a first curved edge portion and a second curved edge portion, and an attachment surface having a concave edge portion joined to the second curved edge portion of the concave surface. The concave surface and the attachment surface are disposed at an angle. The glenoid cutting guide includes a body having a convex surface engageable with a surface of a glenoid cavity and a cutting guide surface for resecting a cutout in a glenoid cavity, the cutout having a curved edge portion corresponding to the second curved edge portion of the glenoid implant.

In another embodiment, a glenoid implant includes, for example, a body having a concave surface having a first curved edge portion and a second curved edge portion, and an attachment surface having a concave edge portion joined to the second curved edge portion of the concave surface. The concave surface and the attachment surface are disposed at an angle.

In another embodiment, a method for repairing a surface of a glenoid cavity includes, for example, removing a peripheral portion of a glenoid cavity adjacent to a damaged portion of the glenoid cavity using a glenoid cutting guide to form a cutout for receiving a predetermined glenoid implant, securing the predetermined glenoid implant in the cutout, and wherein a concave surface of the glenoid implant corresponds to the removed peripheral surface portion of the glenoid cavity.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

FIG. 9 is an anterior-medial perspective view of the humeral head engaging portion of the glenoid implant of FIG. 4, according to an embodiment of the present disclosure;

FIG. 10 is an anterior-lateral perspective view of the humeral head engaging portion of the glenoid implant of FIG. 4, according to an embodiment of the present disclosure;

FIG. 11 is an anterior-medial perspective view of the support portion of the glenoid implant of FIG. 4, according to an embodiment of the present disclosure;

FIG. 12 is an anterior-lateral perspective view of the support portion of the glenoid implant of FIG. 4, according to an embodiment of the present disclosure;

DETAILED DESCRIPTION

Generally stated, disclosed herein are glenoid implants and glenoid cutting guides. Glenoid implant systems may include one or more glenoid implants along with one or more corresponding glenoid implant cutting guides. Further, surgical methods employing the same are also disclosed.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference.

Positions or directions may be used herein with reference to anatomical structures or surfaces. For example, as the current devices and methods are described herein with reference to use with the bones of the shoulder, the bones of the shoulder may be used to describe the surfaces, positions, directions or orientations of the implant apparatus, implant installation apparatus, and surgical methods. Further, the devices and surgical methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and surgical methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the apparatus and surgical methods, and the aspects, components, features and the like thereof, described herein with respect to a left shoulder may be mirrored so that they likewise function with a right shoulder and vice versa.

Figure 1:
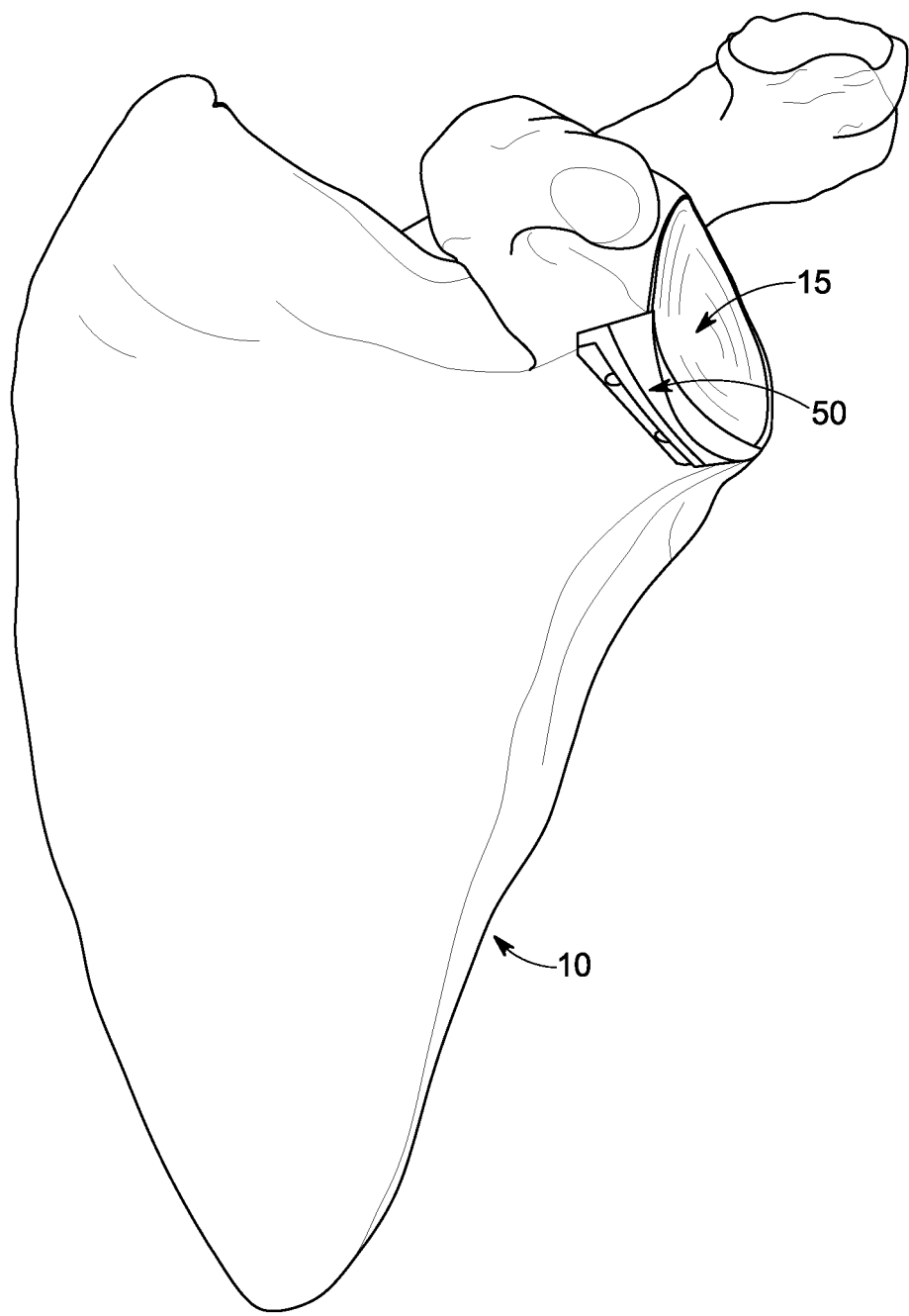
FIG. 1 is a perspective view of a glenoid implant secured to a glenoid cavity, according to an embodiment of the present disclosure.
Figure 2:
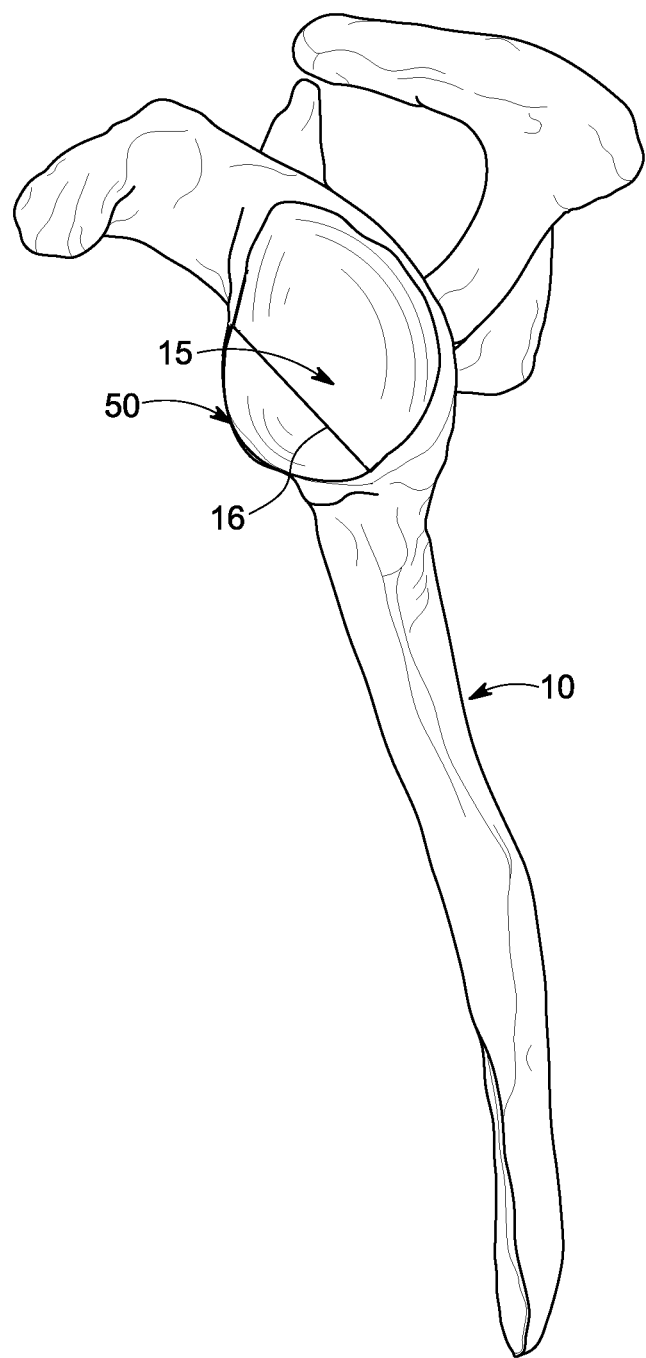
FIG. 2 is a lateral view of the glenoid implant of FIG. 1 secured to a glenoid cavity, according to an embodiment of the present disclosure.
Figure 19:
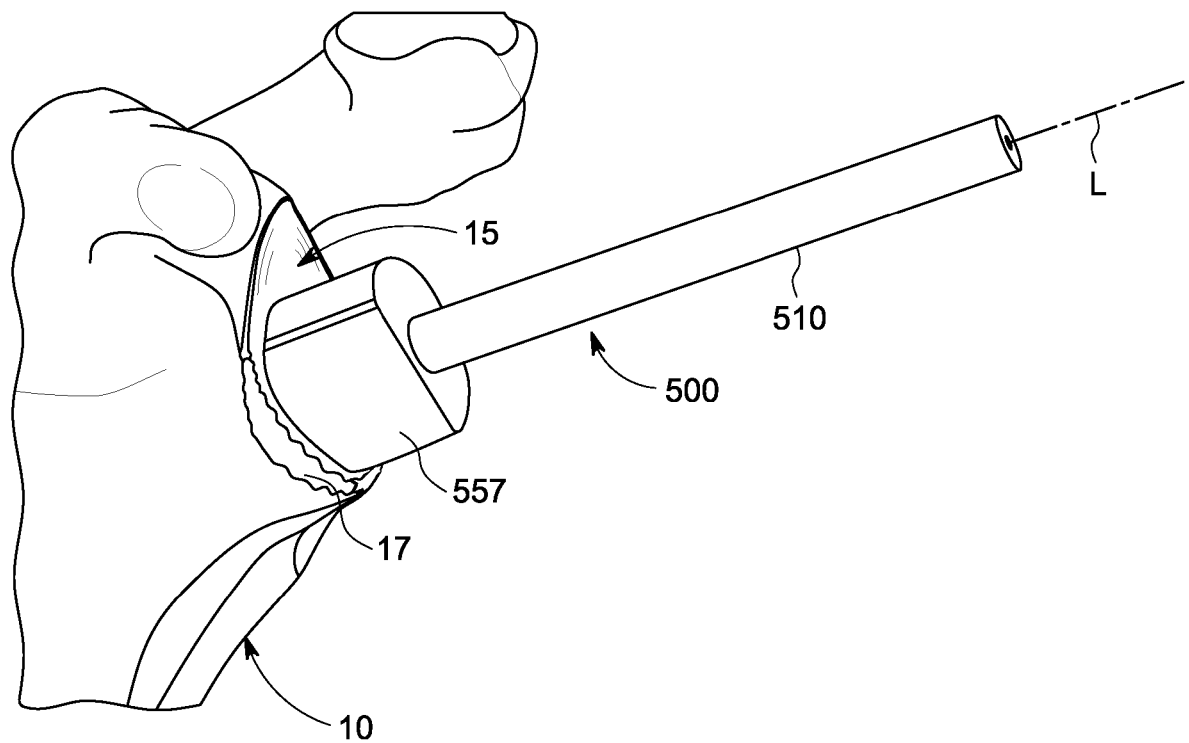
FIG. 19 is a perspective view of the glenoid cutting guide of FIG. 15 disposed against a glenoid cavity prior to resecting a portion of the glenoid cavity adjacent to a damaged portion of the glenoid cavity, according to an embodiment of the present disclosure.

Referring to the drawings, wherein like reference numerals are used to indicate like or analogous components throughout the several views, and with particular reference to FIGS. 1 and 2, there is illustrated an exemplary embodiment of a biocompatible glenoid implant 50 installed and secured in a cutout 20 (FIG. 3) of a glenoid cavity 15 of a scapula 10 such as for repair of a Bankart lesion 17 (FIG. 19). The glenoid implant 50 is designed to restore the normal anatomy of the glenoid cavity in the anteroinferior area of the glenoid cavity of the scapula bone where a Bankart lesion occurs. With reference to FIGS. 15-18, a glenoid cutting guide 500 allows resecting a cutout around a Bankart lesion 17 (FIG. 19) sized for receiving the glenoid implant 50 (FIG. 1). As further described below, glenoid implant systems having a glenoid implant and a glenoid cutting guide of the present disclosure may be designed to fit the various patient anatomies that may be encountered. For example, a plurality of glenoid implants and glenoid cutting guides may be designed in multiple radii of curvature or having different curved surfaces, and depth options to allow for selecting the best fit for a given patient anatomy and corresponding defect.

The glenoid implants for a Bankart lesion can be used in connection with a hemi-arthroplasty or humeral implant apparatus. For example, the present disclosure for the glenoid implants, glenoid cutting guides, and glenoid implant systems for repair of the glenoid may be used in conjunction with the humeral implants, humeral cutting guides, and humeral implant systems for the repair of a Hill-Sachs lesions described in the commonly assigned, co-filed international PCT patent application no: PCT/US2020/013482, filed Jan. 14, 2020, entitled "Implant Systems For Repair Of A Humeral Head" which international PCT patent application claims priority to U.S. provisional patent application No. 62/792,594, filed Jan. 15, 2019, entitled "Implant Systems For Repair Of A Humeral Head", which applications are hereby incorporated herein by reference in their entirety.

As will be appreciated, the present disclosure addresses the problem of recurring instability and dislocation events caused by, for example, the presence of a lesion on the surface of a glenoid cavity (e.g., Bankart lesion) resulting from a traumatic injury (shoulder dislocation). The present disclosure provides a solution to surgeons for the treatment of patients with debilitating instability of the shoulder joint by providing an implantable device or apparatus that correctly replicates the normal anatomy of the affected bone in the shoulder, re-creating the original articular surface geometry. Advantages of the present disclosure may be shorter surgery time compared to conventional glenoid cavity reconstruction.

As shown in FIGS. 4-8, the glenoid implant 50 is designed having a cavity forming portion and an attachment portion. This configuration allows for the repair of a glenoid cavity, for example, due to a Bankart lesion.

Figure 4:
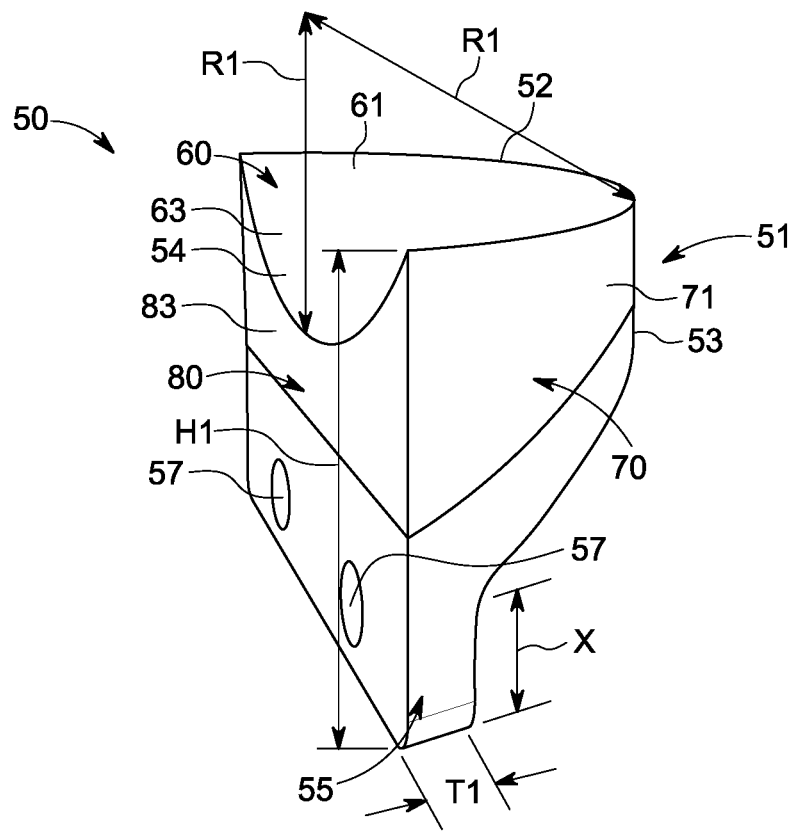
FIG. 4 is an enlarged anterior-medial perspective view of the glenoid implant of FIG. 1, according to an embodiment of the present disclosure.
Figure 5:
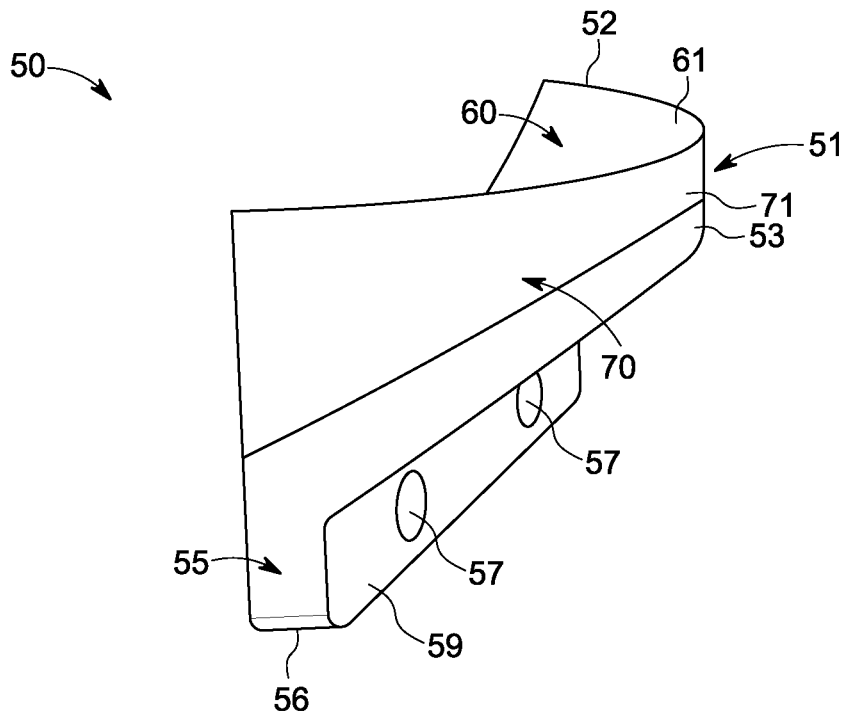
FIG. 5 is an anterior-lateral perspective view of the glenoid implant of FIG. 4, according to an embodiment of the present disclosure.

With reference to FIGS. 4 and 5, the glenoid implant 50 may include a body 51 having an outwardly extending portion 53 and a flange portion 55. In this illustrated embodiment, the outwardly extending portion 53 may include, for example, a concave surface 60, a convex surface 70, and an attachment (medial) surface 80 (FIG. 4).

Figure 6:
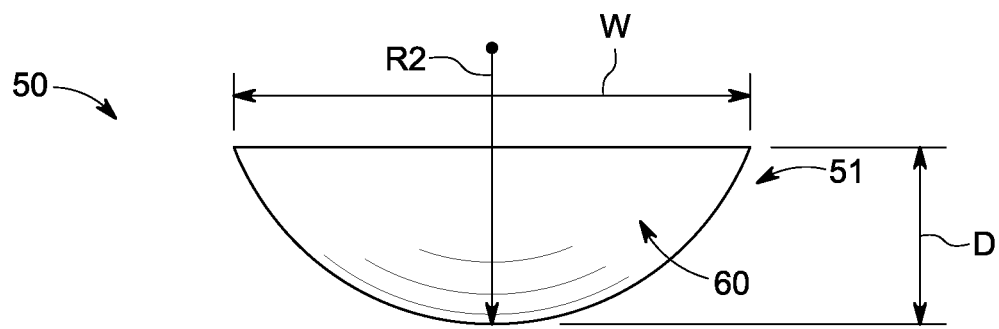
FIG. 6 is a superior view of the glenoid implant of FIG. 4, according to an embodiment of the present disclosure.
Figure 7:
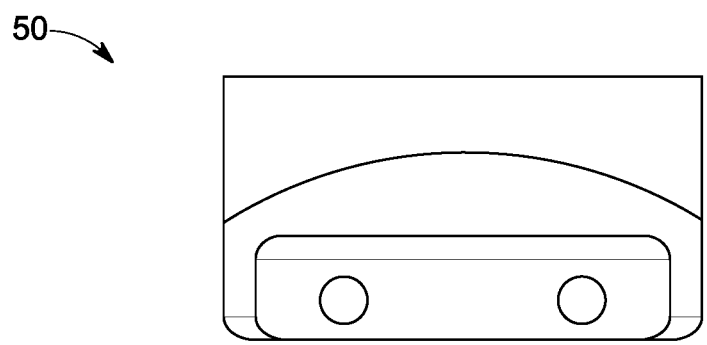
FIG. 7 is a medial elevational view of the glenoid implant of FIG. 4, according to an embodiment of the present disclosure.
Figure 8:
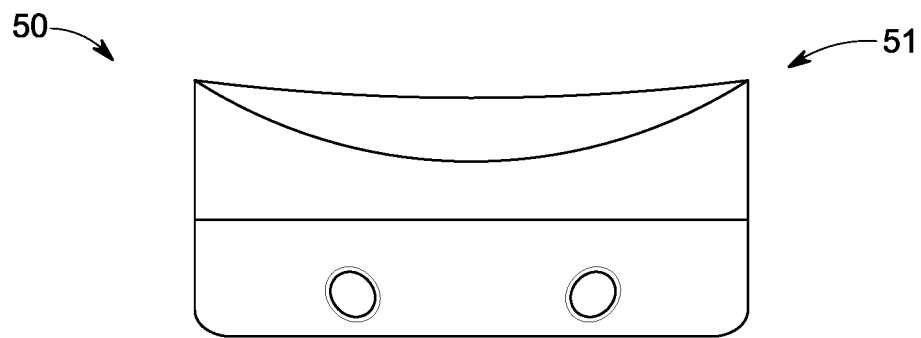
FIG. 8 is a lateral elevational view of the glenoid implant of FIG. 4, according to an embodiment of the present disclosure.

The concave surface 60 may be a generally concave surface that provides an articulating surface against a corresponding humeral head surface. The concave surface 60 may include a first curved edge portion 61 joined to an upper curved edge portion 71 of the first surface 70. The edge portions may define an edge 52 that corresponds to an outer ridge portion or rim of a glenoid cavity. The concave surface 60 may have a constant radius R1 (FIG. 4) or may be a non-constant curved surface. The convex surface 70 may have constant radius R2 as shown in FIG. 6 or may be a non-constant curved surface. The glenoid implant 50 may have a depth D.

With reference again to FIG. 4, the attachment surface 80 may have an upper curved edge portion 83 joined to a second curved edge portion 63 of the concave surface 60. As described in greater detail below, the edge portions may define an edge 54 that abuts and aligns, matches, or is otherwise congruent with an upper cut concave edge 16 (FIG. 2) of the glenoid cavity. The concave surface 60 may be disposed at an angle relative to the attachment surface 80. For example, the edge 52 of concave surface 60 may be disposed along a first plane and at an angle of 90 degrees or other suitable angle relative to the edge 54 and the attachment surface 80 disposed along a second plane. In other embodiments, the attachment surface 80 may be non-planar and/or have other configurations other than flat or planar, and may be disposed at other orientations or varying orientations relative to a concave surface.

With reference again to FIGS. 4 and 5, the glenoid implant 50 may include the flange portion 55 that extends from the outwardly extending portion 53. The flange portion 55 may have a thickness T1 (FIG. 4) and extend a distance X (FIG. 4) from the outwardly extending portion 53. The flange 55 may include a plurality of apertures 57 extending from attachment surface 80 (FIG. 4) to an opposite side 59 (FIG. 5) of the flange 55. The apertures 57 may allow for fixation of the glenoid implant 50 to the bone cutout in the glenoid cavity. For example, a plurality of screws, pins, or other connecting members or devices (not shown) may be passed through one or more of the apertures and into the scapula forming the glenoid cavity.

As shown in FIGS. 9-12, in this illustrated embodiment, the glenoid implant 50 (FIGS. 4 and 5) may be formed from a plurality of different components. For example, the glenoid implant 50 (FIGS. 4 and 5) may include a humeral head engaging portion 100 (FIGS. 9 and 10) and a support portion 200 (FIGS. 11 and 12) formed from different materials and/or similar materials having different characteristics.

In this illustrated embodiment, with reference to FIGS. 9 and 10, the humeral head engaging portion 100 includes concave surface 60 (FIG. 9) and a spaced apart angled surface 115 best shown in FIG. 10. The humeral head engaging portion 100 forms a portion of outwardly-extending portion 70 (FIGS. 4 and 5) of the glenoid implant 50 (FIGS. 4 and 5).

With reference to FIGS. 11 and 12, the support portion 200 may include a cantilevered support portion 210 and a flange portion 220. The cantilevered support portion 210 defines a portion of the outwardly-extending portion 70 (FIGS. 4 and 5) of the glenoid implant 50 (FIGS. 4 and 5), which portion is spaced apart from the concave surface 60 (FIG. 9). The cantilevered support portion 210 defines a surface 215 (FIG. 11) for attaching to the supporting surface 115 (FIG. 10) of the humeral head engaging portion 100 (FIG. 10). The surface 115 (FIG. 10) of the humeral head engaging portion 100 (FIG. 10) and the surface 215 (FIG. 11) of the cantilevered support portion 210 (FIG. 11) may be disposed at an angle A (FIGS. 9 and 11) relative to surfaces 125 (FIG. 9) of the humeral head engaging portion 100 (FIG. 9) and surface 225 (FIG. 11) of the support portion 200 (FIG. 9).

In this illustrated embodiment, the humeral head engaging portion 100 may be made of a polymeric material such as UHMWPE, polyurethane, PEEK, or a hydrogel. Further examples of suitable polymeric materials are described in U.S. Pat. No. 7,662,954, issued to James, et al., entitled "Outer Layer Having Entanglement Of Hydrophobic Polymer Host And Hydrophilic Polymer Guest", which is incorporated herein by reference in its entirety. For example, an outer layer of the humeral head engaging portion may be a material which include a hydrophobic polymer host that is a water-insoluble hydrocarbon-based polymer, and a hydrophilic guest, wherein the hydrophilic guest includes hyaluronic acid. The material further includes crosslinked molecules of the hydrophilic guest with the guest, and a hydrophilic bearing outer surface of the layer, adapted for mechanical wear, comprising hydrophilic functional groups.

In another embodiment, an outer layer of the humeral head engaging portion may be a material, which includes a hydrophobic polymer host and a hydrophilic guest, wherein the hydrophilic guest comprises hyaluronic acid. The material includes crosslinked molecules of the hydrophilic guest with the guest, and a hydrophilic outer surface of the layer that includes hydrophilic functional groups, wherein the hydrophobic polymer host is a water-insoluble hydrocarbon-based polymer. In another embodiment, an outer layer of the humeral head engaging portion may be a material, which includes a hydrophobic polymer host and a hydrophilic guest, wherein the hydrophilic guest comprises hyaluronic acid, and wherein the material includes crosslinked molecules of the hydrophilic guest with the guest. The layer further includes a hydrophilic outer surface of the hydrophilic functional groups, and wherein: the hydrophobic polymer host is a water-insoluble hydrocarbon-based polymer having a porous polymeric structure, and a portion of the crosslinked molecules of the guest is located within the pores of the porous host structure. In another embodiment, an outer layer of the humeral head engaging portion may be a material, which includes a hydrophobic polymer host and a hydrophilic guest, wherein the hydrophilic guest includes hyaluronic acid. The material includes crosslinked molecules of the hydrophilic guest with the guest. A hydrophilic outer surface of the layer includes hydrophilic functional groups, and wherein the host and guest are in powdered form, and, the hydrophilic outer surface of the outer layer is a thermal molding of the powdered form of the guest with the hydrophobic polymer host, wherein the hydrophobic polymer host is a water-insoluble hydrocarbon-based polymer. In the various embodiment, the water-insoluble hydrocarbon-based polymer may be an ultra-high molecular weight polyethylene (UHMWPE).

The concave surface 60 of the humeral head engaging portion 100 may be machined to create a contour that closely matches the curvature and shape of the normal articulating surface of a portion of the glenoid cavity. In other embodiments, the implant or body of the glenoid implant may be molded to shape. The humeral head engaging portion 100 may be solid and not hollow, or may include one or more hollow portions or cavities.

The support portion 200 of the glenoid implant may be made out of a standard metallic implant material, such as titanium, cobalt chrome, or other acceptable stainless steels. In some embodiments, the polymeric humeral head engaging portion 100 may be molded onto the support portion.

Figure 13:
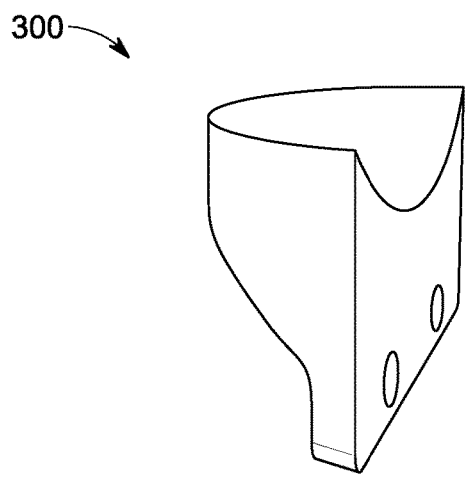
FIG. 13 is a posterior-medial perspective view of another glenoid implant, according to an embodiment of the present disclosure.

FIG. 13 illustrates a glenoid implant 300, according to an embodiment of the present disclosure. The glenoid implant 300 may be a one-piece, integral, or monolithic structure formed from a single material. The configuration of glenoid implant 300 may be essentially the same as the glenoid implant 50 (FIGS. 4 and 5) described above. In this illustrated embodiment, the glenoid implant 300 may be made entirely from a polymeric material or metallic material such as described above. In other embodiments, a glenoid implant may be formed from three or more different materials or material having different characteristics.

Figure 3:
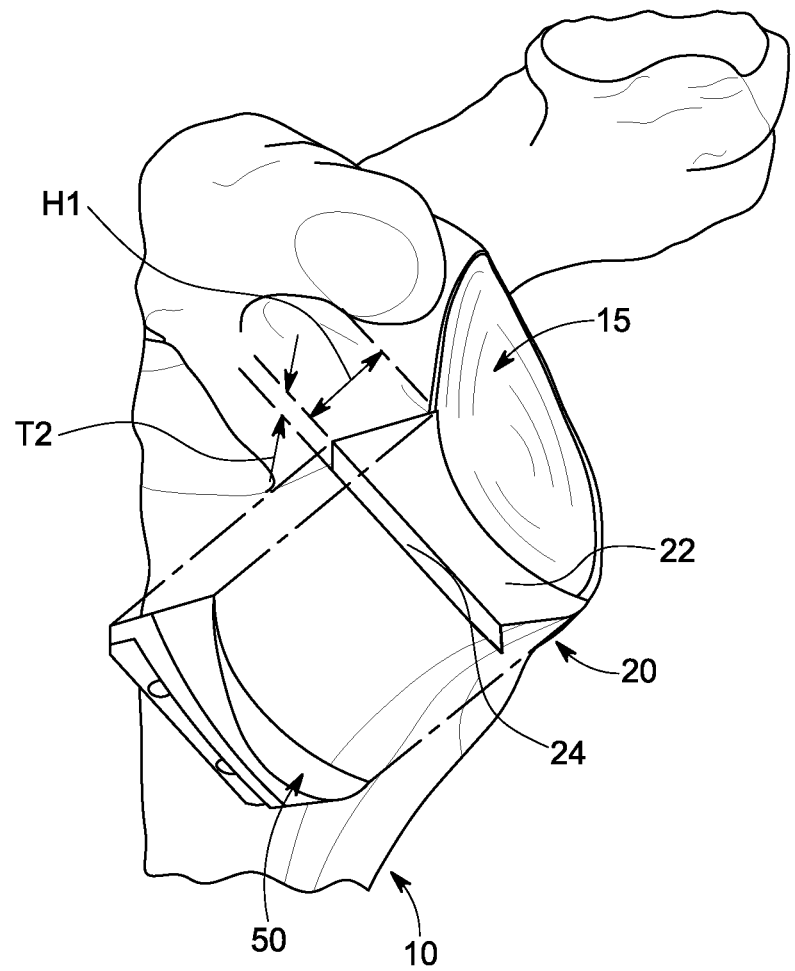
FIG. 3 is an enlarged, exploded perspective view of the glenoid cavity of FIG. 1 with the glenoid implant removed illustrating a cutout in the glenoid cavity, according to an embodiment of the present disclosure.

The sides of the glenoid implant apparatus that interact with the bone, e.g., the attachment surface 80 and the bottom of the flange, may have a surface treatment such as porous coating, HA coating, titanium plasma spray, or grit blasting, which will allow for a higher coefficient of friction to better fix the glenoid implant in, as shown in FIG. 3, the cutout 20 of the glenoid cavity and promote bone in growth. The glenoid implant may be affixed to the glenoid cavity with pins, stems, screws, or a combination thereof in order to prevent movement, prevent the glenoid implant from sliding out of the prepared cutout site in the scapula, and facilitate bone in growth.

The glenoid implants may be designed in multiple sizes to allow selection by a surgeon based on the configuration of the particular lesion being treated. For example, FIG. 14 illustrates lateral elevational views of a plurality of differently sized and shaped implants that may be provided based on the normal surface anatomy of the glenoid cavity and the typical locations of the lesions, and which may include for example, two outer radius options, each with 4 inner radius of curvature options, and two depth options, which correspond to Table 1 below.

TABLE 1

| | Outer Radius | Inner Radius | Depth |
|---|---|---|---|
| a) | 25 mm | 20 mm | 7.5 mm |
| b) | 25 mm | 23 mm | 7.5 mm |
| c) | 25 mm | 26 mm | 7.5 mm |
| d) | 25 mm | 28 mm | 7.5 mm |
| e) | 30 mm | 20 mm | 9 mm |
| f) | 30 mm | 23 mm | 9 mm |
| g) | 30 mm | 26 mm | 9 mm |
| h) | 30 mm | 28 mm | 9 mm |

Figure 14:
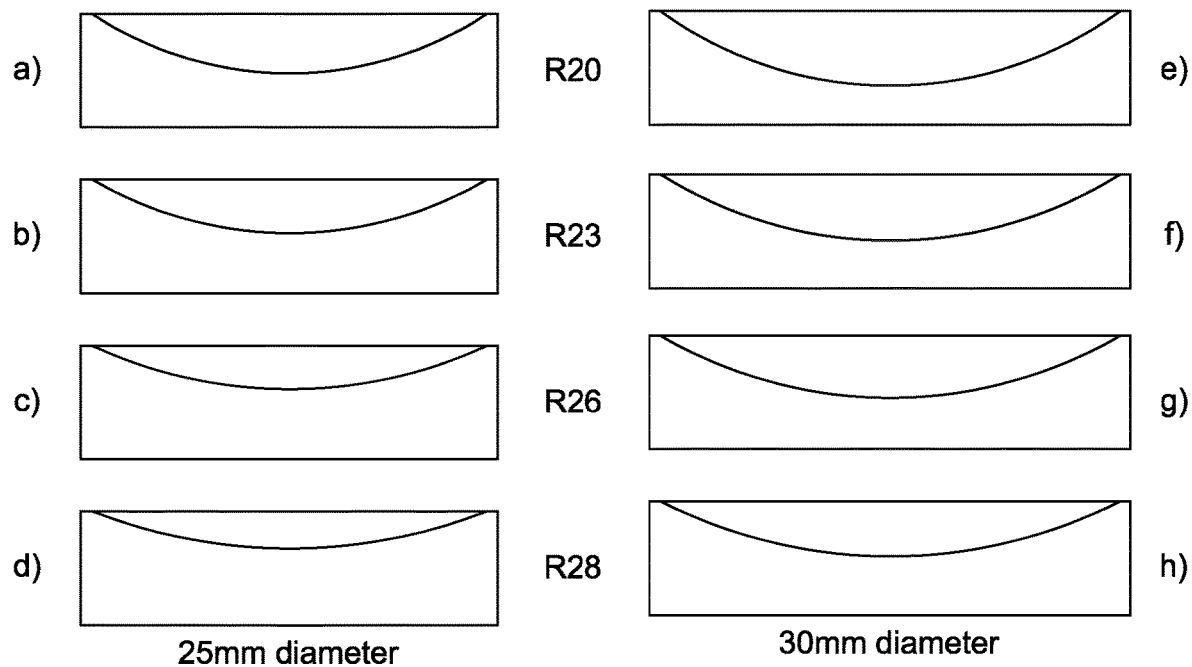
FIG. 14 illustrate representative superior views of glenoid implants, according to embodiments of the present disclosure.

As is shown in FIG. 14, in moving from the left column to right column the outer radius (see, for example, radius R2 in FIG. 6), and the depth (see, for example, depth D in FIG. 6) increases. In moving from the top row to the bottom row, the inner radius of curvature (see, for example, radius R1 in FIG. 4) increases. While 8 different implants sizes and configurations are illustrated, it will be appreciated that fewer or more differently sized and configured implants may be acceptable in covering the typical range of different sized and shaped humeral heads.

FIGS. 15-18 illustrate the glenoid cutting guide 500, according to an embodiment of the present disclosure for facilitating the preparation of the glenoid cavity to receive the preconfigured, pre-sized glenoid implant. The glenoid cutting guide 500 may be used to assess the size and the location of the lesion, as well as provide a guide surface for cutting the scapula adjacent to the lesion. As described below, different sized glenoid cutting guides may be provided, which fit the size and configuration of the glenoid cavity and the lesion to form a specifically sized cutout that corresponds to the size and configuration of the glenoid implant to be installed in the cutout in the glenoid cavity.

Figure 15:
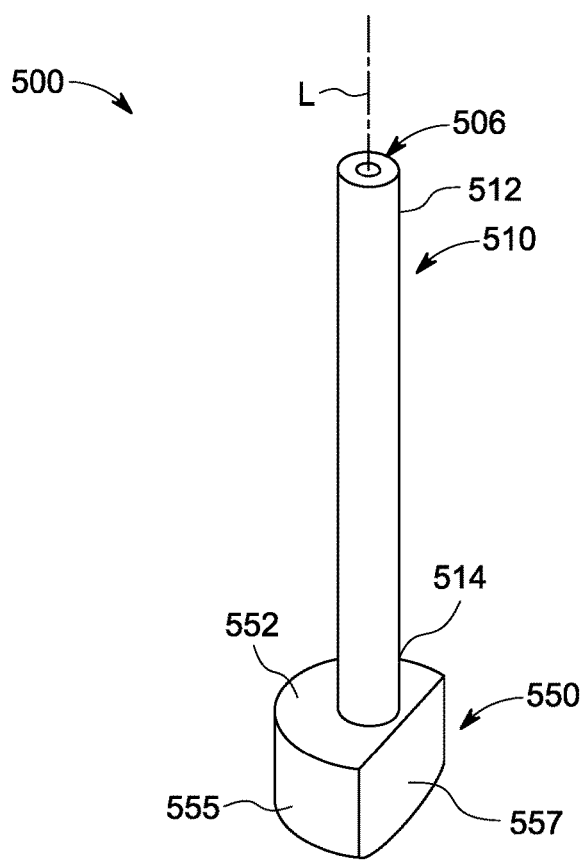
FIG. 15 is a top perspective view of a glenoid cutting guide, according to an embodiment of the present disclosure.
Figure 16:
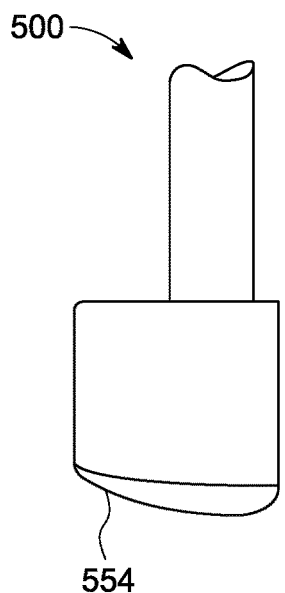
FIG. 16 is a left side elevational view of the glenoid cutting guide of FIG. 15, according to an embodiment of the present disclosure.
Figure 17:
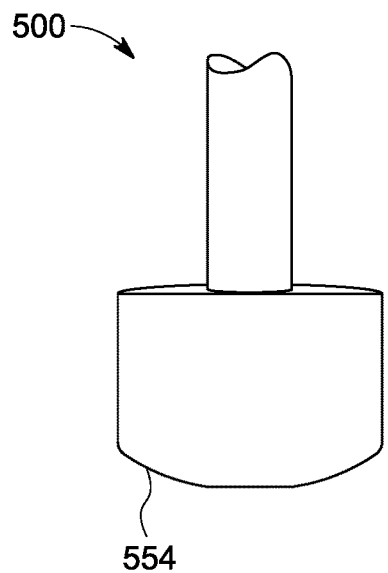
FIG. 17 a rear elevational view of the glenoid cutting guide of FIG. 15, according to an embodiment of the present disclosure.
Figure 18:
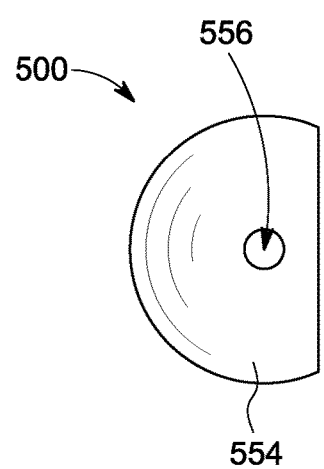
FIG. 18 a bottom view of the glenoid cutting guide of FIG. 15, according to an embodiment of the present disclosure.

As shown in FIG. 15, the glenoid cutting guide 500 includes an elongated positioning guide 510 and an enlarged body 550. Elongated positioning guide 510 may include a hollow cylindrical member having a first end 514, a second end 512, and a passageway 506 extending therethrough. The passageway 506 may define a longitudinal axis L.

The enlarged body 550 may include a top surface 552, a convex lower surface 554 (FIG. 16), a partial cylindrical outer surface 555, and a cutting guide surface 557. A passageway 556 (FIG. 18) disposed in the body 550 may be aligned with the passageway 506 in elongated positioning guide 510. The guide is rotated about its longitudinal axis L until the cutting guide surface 557 is aligned with the lesion. The cutting guide surface 557 may be a flat or a planar surface and is intended to guide a cut to resect the bone immediately adjacent or around the lesion, for example, with a flat saw blade when the glenoid cutting guide is placed against the glenoid cavity surface adjacent to, for example, a Bankart lesion 17 as shown in FIG. 19. The cutting guide surface 557 may be disposed parallel to the longitudinal axis L and to the outer elongated surface of elongated member 510 of glenoid cutting guide 500. Suitable cutting tools may be employed to resect the glenoid cavity, for example, a chisel, a milling tool, or an oscillating saw blade.

Figure 20:
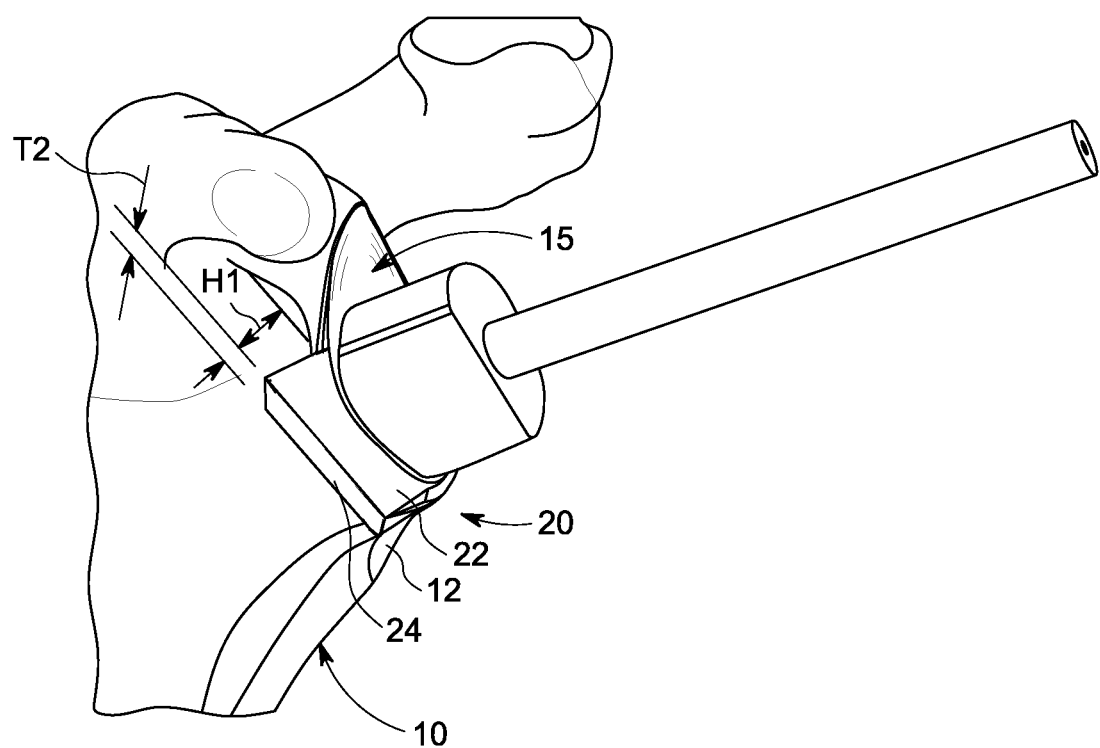
FIG. 20 is a perspective view of the glenoid cutting guide of FIG. 15 disposed against a glenoid cavity after resecting a portion of the glenoid cavity, according to an embodiment of the present disclosure.

For example, a plurality of different glenoid cutting guides 500, each having a different configuration, e.g., inner curved concave surface, outer diameter of the body, and position of the cutting guide surface, may be provided for covering the typical range of the different sizes of patients' glenoid cavities such as portions of the glenoid cavities prone to lesions. Once a surgeon determines the suitable glenoid cutting guide, the surgeon can position the glenoid cutting guide 500 relative to the lesion observable adjacent to the cutting guide surface 557. The glenoid cutting guide 500 may be used by a surgeon holding the glenoid cutting guide 500 in position against the glenoid cavity when cutting the glenoid cavity. Alternatively, a surgeon may insert a pilot nail (not shown) through the passageway 506 (FIG. 15) in the elongated member 510 (FIG. 15) and passageway 556 (FIG. 18) in the body 550 (FIG. 18) and into the glenoid cavity for securing the glenoid cutting guide 500 to the glenoid cavity during the cutting of the glenoid cavity adjacent to a lesion 15 (FIG. 19). Securing the glenoid cutting guide to a glenoid cavity via a pilot nail limits movement of the cutting apparatus 500 across the surface of the glenoid cavity during the cutting procedure while the surgeon holds the elongated member 510 to prevent rotation. As shown in FIG. 20, the cutting procedure removes a portion of the glenoid cavity 15 and a portion of the infraglenoid tubercle 12. In other embodiments, suitable configured glenoid cutting guides and glenoid implants may be operable for repairing other portions around the periphery of the glenoid cavity due to lesions.

The glenoid cutting guide 500, in some embodiments, is designed to fit onto the lower portion of the glenoid cavity. The glenoid cutting guide 500 may include a slot or planar edge feature that is operable to control the height and the thickness of the cut to ensure the correct fit of a corresponding selected glenoid implant. For example, in some embodiments, the body may have a cylindrical diameter of about 25 millimeters to 30 millimeters.

With reference again to FIGS. 3 and 20, for example, the cutout 20 may include a first surface 22 extending downwardly from the glenoid cavity 15 and a second surface 24. A width T2 of the second surface 24 may be the same, less than, or greater than a thickness T1 (FIG. 4) of the glenoid flange portion 55 (FIG. 4) of glenoid implant 50 (FIG. 4). A height H1 of the first surface 22 may be the same or greater than a height H1 (FIG. 4) of the glenoid implant 50 (FIG. 4). The glenoid implant 50 (FIG. 3) may be pushed against surfaces 22 and 24 to seat the entirety of the glenoid implant 50 (FIG. 1) in the cutout 20 of the scapula, forming the glenoid cavity. For example, second surface 24 may act as a stop or landing for engaging lower surface 56 (FIG. 5) of the glenoid flange portion 55 (FIG. 5). In some embodiments, depending on the shape of the bone adjacent to the glenoid cavity, surface 22 may blend into the bone so that little or no second surface 24 is provided. In other embodiments, a surgeon may saw the glenoid cavity so that the second surface 24 is provided with a clearance or gap between the lower surface 56 (FIG. 5) of the glenoid flange portion 55 (FIG. 5). Screws, pins or other connectors may be installed in apertures 57 (FIG. 5) to prevent movement of the glenoid implant out of the cutout. In other embodiments, the glenoid implants may include one or more posts, for example, extending from the flat surface of the glenoid implant, resulting in one or more posts being receivable in one or more holes disposed on surface 22 of the scapula and operable to hold the glenoid implant in place.

With reference again to FIG. 15, the elongated positioning guide 510 of glenoid cutting guide 500 may be a one-piece, integral, or monolithic structure formed from a single material. The body may be formed from an engineering plastic material or a stainless steel material. The body 550 may be a one-piece, integral, or monolithic structure formed from a single material. The body may be formed from an engineering plastic material or a stainless steel material. The elongated positioning guide 510 and body 550 may be operably connected to form the glenoid cutting guide 500. In other embodiments, the glenoid cutting guide apparatus 500 may be a one-piece, integral, or monolithic structure, or may be formed from a plurality of separate components.

Figure 21:
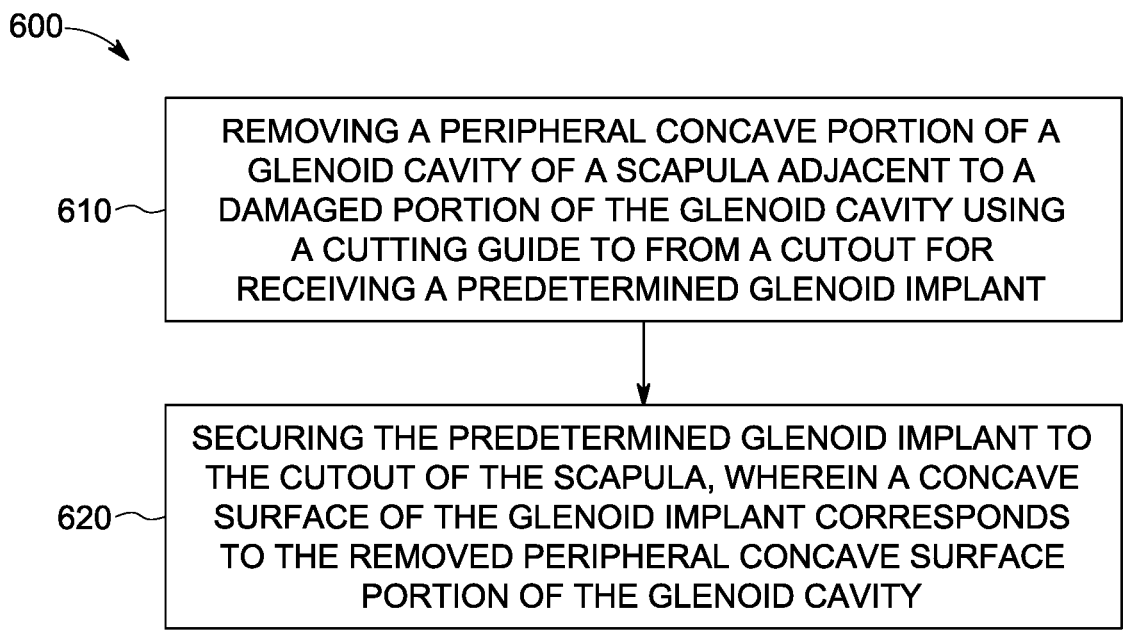
FIG. 21 is a flowchart of a process for repairing a glenoid cavity, according to an embodiment of the present disclosure.

FIG. 21 illustrates a method 600 for repairing a glenoid cavity having a lesion, according to an embodiment of the present disclosure. The method 600 may include, for example, at 610 removing a peripheral concave portion of a glenoid cavity of a scapula adjacent to a damaged portion of the glenoid cavity using a glenoid cutting guide to form a cutout for receiving a predetermined glenoid implant, and at 620 securing the predetermined glenoid implant in the cutout of the scapula, wherein a concave surface of the glenoid implant corresponds to the removed peripheral concave surface portion of the glenoid cavity.

While a flat planar cutting surface is illustrated on the glenoid cutting guide for forming a flat attachment surface for engaging the corresponding surface of the glenoid implant, it will be appreciated that other shaped surfaces may be employed. For example, the cutting surface may include two angled planar surfaces or other suitable configurations.

The technique of the present disclosure may allow replacing about 25 percent of the glenoid cavity due to a lesion.

Benefits of the present disclosure include efficiently providing a repair of a Bankart lesions in a glenoid cavity that may allow for greater range of motion compared to bone grafts (e.g., iliac crest) or with a Latarjet surgical technique. For example, the present disclosure overcomes the problem of Latarjet procedures requiring resection and/or relocation of the tissues around the shoulder joint, which alters the normal biomechanics of the joint and can have the effect of reducing range of motion after surgery. The present technique may also overcome the potential risk of graft failure. Further benefits of the present disclosure may include shorter surgery time (no need to resect tip of coracoid process), and minimal bone resection as the glenoid implant is selected based on the lesions being repaired. The technique of the present disclosure solves the problem by providing an implantable device that correctly replicates the normal anatomy of the affected bone in the shoulder, re-creating the original articular surface geometry.

The glenoid implant may be designed in multiple radii of curvature options to allow for selecting the best fit for a given patient anatomy. The glenoid implant may also be designed in multiple sizes to allow selection based on the size of the particular lesion being treated. The glenoid implant contains features that allow for screws to pass through for fixation to the glenoid bone. The glenoid cutting guide provides a sizing instrument to assist in determination of the correct glenoid implant size, and selection of the desired corresponding predetermined or prefabricated glenoid implant.

As may be recognized by those of ordinary skill in the art based on the teachings herein, numerous changes and modifications may be made to the above-described and other embodiments of the present invention without departing from the scope of the invention. The implants, screws, and other components of the devices and/or apparatus as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and apparatus may include more or fewer components or features than the embodiments as described and illustrated herein. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general apparatus operation. Modifications and alterations will occur to others upon a reading and understanding of the preceding detailed description. It is intended that the invention be construed as including all such modifications and alterations.

The invention claimed is:

1. A glenoid implant system for repair of a glenoid cavity of a patient, the glenoid cavity having a surface, said glenoid implant system comprising:
   a glenoid implant comprising a body having:
      a concave surface with a first curved edge portion and a second curved edge portion;
      an attachment surface having a concave edge portion joined to said second curved edge portion of said concave surface; and
      wherein said concave surface and said attachment surface are disposed at an angle; and
   a glenoid cutting guide having a body having a convex surface configured to be engageable with the surface of the glenoid cavity and a cutting guide surface configured for resecting a cutout in the glenoid cavity; and
   said second curved edge portion of said glenoid implant configured to correspond to a curved edge portion of the cutout in the glenoid cavity, and said attachment surface of the glenoid implant configured to correspond to a surface of the cutout in the glenoid cavity.

2. The glenoid implant system of claim 1, wherein said first curved edge portion is disposed at 90 degrees relative to said second curved edge portion.

3. The glenoid implant system of claim 1, wherein said first curved edge portion is disposed at 90 degrees relative to said attachment surface.

4. The glenoid implant system of claim 1, wherein said first curved edge portion comprises a first radius, and said second curved edge portion comprises a second radius different from said first radius.

5. The glenoid implant system of claim 1, wherein said body comprises an outwardly extending portion defining said concave surface and a flange portion extending from said outwardly extending portion and defining a portion of said attachment surface.

6. The glenoid implant system of claim 5, wherein said flange portion comprises a plurality of apertures.

7. The glenoid implant system of claim 1, wherein said glenoid implant comprises a metallic material and/or a polymeric material.

8. The glenoid implant system of claim 1, wherein said glenoid implant comprises a monolithic one-piece glenoid implant.

9. The glenoid implant system of claim 1, wherein said glenoid implant comprises a metallic material defining a cantilevered portion of said support and a flange, and a polymeric material supported by said cantilevered portion, said polymeric material defining said concave surface.

10. The glenoid implant system of claim 9, wherein said flange comprises a plurality of apertures.

11. The glenoid implant system of claim 1, wherein said cutting guide surface of said glenoid cutting guide is disposed normal to said convex surface.

12. The glenoid implant system of claim 1, wherein said cutting guide surface of said glenoid cutting guide comprises a planar surface.

13. The glenoid implant system of claim 1, wherein said glenoid cutting guide comprises an elongated member having a first end and a second end, said first end attached to said body of said glenoid cutting guide.

14. The glenoid implant system of claim 13, wherein said glenoid cutting guide comprises a first passageway extending through said elongated member, a second passageway extending through said body and opening onto said convex surface of said glenoid cutting guide, and said first passageway aligned with said second passageway.

15. A glenoid implant comprising:
a glenoid implant comprising a body having:
a concave surface having a first curved edge portion and a second curved edge portion;
an attachment surface having a concave edge portion joined to said second curved edge portion of said concave surface; and
wherein said concave surface and said attachment surface are disposed at an angle;
wherein said body of said glenoid implant comprises an outwardly-extending cantilevered portion and a flange;
wherein said outwardly-extending cantilevered portion and said flange comprising a metallic material;
wherein said body of said glenoid implant comprising a polymeric material supported by said outwardly-extending cantilevered portion, said polymeric material defining said concave surface.

16. The glenoid implant of claim 15, wherein said first curved edge portion is disposed at 90 degrees relative to said second curved edge portion.

17. The glenoid implant of claim 15, wherein said first curved edge portion is disposed at 90 degrees relative to said attachment surface.

18. The glenoid implant of claim 15, wherein said first curved edge portion comprises a first radius, and said second curved edge portion comprises a second radius different from said first radius.

19. The glenoid implant of claim 15, wherein said flange portion comprises a plurality of apertures.

20. The glenoid implant of claim 15, wherein said flange comprises at least one aperture.

21. A method for repairing a surface of a glenoid cavity, the method comprising:
providing the glenoid implant of claim 15;
removing a peripheral portion of a glenoid cavity adjacent to a damaged portion of the glenoid cavity using a glenoid cutting guide to form a cutout for receiving the glenoid implant;
securing the glenoid implant in the cutout; and
wherein a concave surface of the glenoid implant corresponds to the removed peripheral surface portion of the glenoid cavity.

22. The method of claim 21, further comprising selecting the glenoid implant from a plurality of glenoid implants having different configurations based on the surface anatomy of the glenoid cavity.

23. The method of claim 21, wherein the glenoid implant comprises a metal and/or polymeric material.

24. The glenoid implant system of claim 1, wherein the cutout in the glenoid cavity comprises a stop, and said attachment portion of said glenoid implant is engageable with the stop.

25. The glenoid implant system of claim 1, wherein said glenoid implant comprises a cantilevered portion and a flange, and the cantilever and the flange comprises an angle therebetween greater than 90 degrees.

26. The glenoid implant system of claim 9, wherein the cantilever and the flange comprises an angle therebetween greater than 90 degrees.

27. The glenoid implant of claim 15, wherein the flange is engageable with a cutout in the glenoid cavity comprises a stop.

28. The glenoid implant of claim 15, wherein the cantilever and flange comprises an angle therebetween greater than 90 degrees.

* * * * *